United States Patent
Lovell et al.

(10) Patent No.: US 9,486,581 B2
(45) Date of Patent: Nov. 8, 2016

(54) INJECTOR DEVICE WITH FORCE LOCK-OUT AND INJECTION RATE LIMITING MECHANISMS

(75) Inventors: John Lovell, North Bergen, NJ (US); Robert E. West, Basking Ridge, NJ (US); Todd M. Chelak, Westborough, MA (US); William Easterbrook, Westwood, NJ (US); Mark A. Follman, Glen Rock, NJ (US); Edward P. Browka, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1672 days.

(21) Appl. No.: 11/102,882

(22) Filed: Apr. 11, 2005

(65) Prior Publication Data
US 2006/0229570 A1  Oct. 12, 2006

(51) Int. Cl.
*A61M 5/315* (2006.01)
*A61M 5/20* (2006.01)
*A61M 5/28* (2006.01)
*A61M 5/46* (2006.01)
*A61M 5/32* (2006.01)

(52) U.S. Cl.
CPC ............... *A61M 5/20* (2013.01); *A61M 5/28* (2013.01); *A61M 5/3158* (2013.01); *A61M 5/31551* (2013.01); *A61M 5/46* (2013.01); *A61M 5/315* (2013.01); *A61M 5/31561* (2013.01); *A61M 5/31571* (2013.01); *A61M 5/31593* (2013.01); *A61M 5/3202* (2013.01); *A61M 2005/2013* (2013.01)

(58) Field of Classification Search
CPC ............. A61M 5/488; A61M 5/2033; A61M 2005/208; A61M 2005/2086; A61M 2005/2013; A61M 5/20; A61M 5/28; A61M 5/31551; A61M 5/3158; A61M 5/46
USPC ........ 604/110, 192, 195, 197–198, 207–211, 604/220, 224, 228
See application file for complete search history.

(56) References Cited

U.S. PATENT DOCUMENTS

| | | | | |
|---|---|---|---|---|
| 3,494,358 | A * | 2/1970 | Duesterheft et al. | 604/137 |
| 4,583,978 | A | 4/1986 | Porat et al. | |
| RE32,974 | E | 7/1989 | Porat et al. | |
| 4,865,591 | A * | 9/1989 | Sams | 604/186 |
| 5,078,691 | A | 1/1992 | Hamacher | |
| 5,295,965 | A | 3/1994 | Wilmot | |
| 5,320,609 | A * | 6/1994 | Haber et al. | 604/135 |

(Continued)

FOREIGN PATENT DOCUMENTS

| | | |
|---|---|---|
| GB | 2 331 705 A | 6/1999 |
| WO | WO 02-02179 A1 | 1/2002 |

(Continued)

*Primary Examiner* — Theodore Stigell
(74) *Attorney, Agent, or Firm* — Dickinson Wright PLLC

(57) ABSTRACT

An injectable substance delivery device comprising a pen device body, a cartridge, a plunger, a drive mechanism, and at least one of a lock-out mechanism and a rate-limiting mechanism. The lock-out mechanism is provided through a ratchet engagement between the body and the plunger to restrict plunger movement and to ensure that the required needle puncture depth is realized prior to injection by locking out the injection mechanism from advancing until a specified force is applied to the skin. A rate-limiting mechanism is also provided through a user compressed plunger drive spring to ensure that a specific rate of injection is realized during the injection of a medicament.

49 Claims, 11 Drawing Sheets

(56) References Cited

U.S. PATENT DOCUMENTS

| | | |
|---|---|---|
| 5,378,233 A | 1/1995 | Haber et al. |
| 5,478,316 A | 12/1995 | Bitdinger et al. |
| 5,505,694 A | 4/1996 | Hubbard et al. |
| 5,632,730 A * | 5/1997 | Reinert ............... 604/137 |
| 5,658,259 A | 8/1997 | Pearson et al. |
| 5,681,291 A | 10/1997 | Galli |
| 6,093,172 A | 7/2000 | Funderburk et al. |
| 6,293,925 B1 | 9/2001 | Safabash et al. |
| 6,494,865 B1 | 12/2002 | Alchas |
| 6,544,234 B1 | 4/2003 | Gabriel |
| 6,558,402 B1 | 5/2003 | Chelak et al. |
| 6,569,143 B2 | 5/2003 | Alchas et al. |
| 6,575,939 B1 | 6/2003 | Brunel |
| 6,589,209 B1 | 7/2003 | Dysarz |
| 6,607,508 B2 * | 8/2003 | Knauer ............... 604/131 |
| 6,607,509 B2 | 8/2003 | Bobroff et al. |
| 6,620,137 B2 | 9/2003 | Kirchhofer et al. |
| 6,767,336 B1 | 7/2004 | Kaplan |
| 6,805,686 B1 | 10/2004 | Fathallah et al. |
| 6,830,560 B1 | 12/2004 | Gross et al. |
| 6,830,562 B2 | 12/2004 | Mogensen et al. |
| 6,979,316 B1 | 12/2005 | Rubin et al. |
| 6,997,907 B2 | 2/2006 | Safabash et al. |
| 7,112,187 B2 | 9/2006 | Karlsson |
| 7,118,553 B2 | 10/2006 | Scherer |
| 7,207,974 B2 | 4/2007 | Safabash et al. |
| 7,252,651 B2 | 8/2007 | Haider et al. |
| 7,297,136 B2 | 11/2007 | Wyrick |
| 7,309,327 B2 | 12/2007 | Kirchhofer et al. |
| 7,318,816 B2 | 1/2008 | Bobroff et al. |
| 7,329,239 B2 | 2/2008 | Safabash et al. |
| 7,442,185 B2 | 10/2008 | Amark et al. |
| 2002/0007142 A1 * | 1/2002 | Hjertman et al. ............... 604/38 |
| 2003/0050602 A1 | 3/2003 | Pettis et al. |
| 2003/0109829 A1 | 6/2003 | Mogensen et al. |
| 2003/0199823 A1 | 10/2003 | Bobroff et al. |
| 2004/0002682 A1 | 1/2004 | Kovelman et al. |
| 2004/0039336 A1 | 2/2004 | Amark et al. |
| 2004/0039337 A1 | 2/2004 | Letzing |
| 2004/0204687 A1 | 10/2004 | Mogensen et al. |
| 2004/0215151 A1 | 10/2004 | Marshall et al. |
| 2004/0225262 A1 | 11/2004 | Fathallah et al. |
| 2004/0254526 A1 | 12/2004 | Weston |
| 2005/0027255 A1 * | 2/2005 | Lavi et al. .................. 604/135 |
| 2005/0043687 A1 | 2/2005 | Mogensen et al. |
| 2005/0101912 A1 | 5/2005 | Faust et al. |
| 2005/0101919 A1 | 5/2005 | Brunnberg |
| 2005/0203466 A1 | 9/2005 | Hommann et al. |
| 2005/0209569 A1 | 9/2005 | Ishikawa et al. |
| 2005/0222539 A1 | 10/2005 | Gonzales et al. |
| 2006/0030819 A1 | 2/2006 | Young et al. |
| 2006/0149190 A1 | 7/2006 | Kohlbrenner et al. |
| 2006/0178630 A1 | 8/2006 | Bostrom et al. |
| 2006/0189938 A1 | 8/2006 | Hommann et al. |
| 2006/0224124 A1 | 10/2006 | Scherer |
| 2006/0264830 A1 | 11/2006 | Hommann |
| 2006/0270985 A1 | 11/2006 | Hommann et al. |
| 2007/0021720 A1 | 1/2007 | Guillermo |
| 2007/0027430 A1 | 2/2007 | Hommann |
| 2007/0106227 A1 | 5/2007 | Burren et al. |
| 2007/0112310 A1 | 5/2007 | Lavi et al. |
| 2007/0118081 A1 | 5/2007 | Daily et al. |
| 2007/0129686 A1 | 6/2007 | Daily et al. |
| 2007/0129687 A1 | 6/2007 | Marshall et al. |
| 2007/0135767 A1 | 6/2007 | Gillespie, III et al. |
| 2007/0142787 A1 | 6/2007 | Scherer |
| 2007/0191780 A1 | 8/2007 | Modi |
| 2007/0197975 A1 | 8/2007 | Burren et al. |
| 2007/0239117 A1 | 10/2007 | Chelak et al. |
| 2007/0265568 A1 | 11/2007 | Tsals et al. |
| 2007/0270750 A1 | 11/2007 | Dacquay et al. |
| 2008/0009807 A1 | 1/2008 | Hommann |
| 2008/0021390 A1 | 1/2008 | Haider et al. |
| 2008/0039795 A1 | 2/2008 | Slate et al. |
| 2008/0077084 A1 | 3/2008 | Hommann |
| 2008/0077090 A1 | 3/2008 | Hommann |

FOREIGN PATENT DOCUMENTS

| | | |
|---|---|---|
| WO | WO 2004-108193 A1 | 12/2004 |
| WO | WO 2005-009515 A1 | 2/2005 |
| WO | WO 2005-025641 A2 | 3/2005 |
| WO | WO 2005/113039 A1 | 12/2005 |
| WO | WO 2006/057604 A1 | 6/2006 |

* cited by examiner

INJECTOR DEVICE WITH FORCE LOCK-OUT AND INJECTION RATE LIMITING MECHANISMS

CROSS-REFERENCE TO RELATED APPLICATIONS

This application contains subject matter related to that disclosed in a U.S. patent application of Pettis et al., entitled "Microneedle-Based Pen Device For Drug Delivery And Method For Using Same", Ser. No. 10/238,958, filed on Sep. 11, 2002, and in a U.S. patent application of Marsh et al., entitled "Injection Device With Secondary Reservoir", filed concurrently herewith, the entire content of each application being incorporated herein by reference.

FIELD OF THE INVENTION

The present invention relates generally to substance delivery devices. Specifically, one implementation of the invention relates to an injection device and method that incorporates a lock-out mechanism to prevent or minimize leakage of medicament during and after delivery by ensuring proper contact with the skin surface prior to activation.

BACKGROUND OF THE INVENTION

Currently, several injection systems are commercially available for subcutaneous substance delivery of medication. Pen-type injection systems typically use 29 to 31 gauge needles having lengths of between about 5 mm and 12.7 mm, and are used to deliver the contents of a medication cartridge, such as insulin, to the subcutaneous tissue layers of a patient rapidly and conveniently. Additional details of intradermal drug delivery have been previously described in U.S. patent application Ser. No. 09/835,243, filed Apr. 13, 1999, and Ser. No. 09/417,671 filed Oct. 14, 1999, the entire content of each application being incorporated herein by reference.

A "microneedle" pen system has also been developed that further serves to reduce the pain and sensation to the user normally experienced with subcutaneous substance delivery. Such microneedle drug delivery systems may include shorter needles, typically less than or equal to about 3 mm, and having smaller diameters, typically in the range of between about 30 to 34 gauge or thinner. Such needle length and gauge design combinations are desirable to provide for sharp, yet short, point geometries that can more accurately target substance delivery, thereby permitting controlled delivery to only certain selected tissue, such as the deep intradermal or shallow subcutaneous tissue layers. Current typical pen injection systems used for subcutaneous delivery are not believed to be optimal for use by the general population of self-injectors because of, inter alia, the high backpressures associated with injecting fluid into the intradermal layers of the skin using the microneedles.

To achieve effective delivery in light of higher backpressure, it is desirable to control two factors: the depth accuracy of the injection and the rate of the injection. The delivery of medicament within the narrow depth range of the intradermal tissue layer should first be assured and maintained during injection. Once the depth accuracy is obtained, the rate of injection should be controlled to minimize or eliminate leakage of the medicament. Additional details of intradermal drug delivery and microneedles have been previously described in U.S. Pat. No. 6,494,865, issued on Dec. 17, 2002, U.S. Pat. No. 6,569,143, issued on May 27, 2003, and related U.S. patent application Ser. No. 10/238,958, filed Sep. 11, 2002, all of which are assigned to Becton, Dickinson and Company, and the entire contents of each such patent and application being incorporated herein by reference.

The intradermal tissue layer of the skin is considerably denser than the subcutaneous tissue region. The density of the intradermal tissue space on a particular patient is, in part, a function of the collagen make-up which is affected by the patient's age and the location of the injection site on the patient's body. This increased density of the intradermal tissue layer can create greater backpressure resistance on the injection device than the resistance created when injecting into the subcutaneous tissue region. To overcome the increased backpressure resistance when injecting into the intradermal tissue layer with a conventional pen system, the user or patient must exert greater force or pressure (which could be substantial), on the injector device actuator or employ an injector device incorporating a means for generating a mechanical advantage. In these applications, the injector device should preferably be designed to withstand the greater backpressure from the intradermal injection site, as well as facilitate the use of additional force or pressure exerted by the user or patient. It must be noted that the increased fluid pressure of the medicament required to actuate the injector device, if not carefully controlled, may result in "jetting" the medicament past the desired tissue depth, which would be undesirable.

Conventional pen-type injection systems may also require that the user keep the needle seated in the skin for a period of up to 10 seconds to allow the "axial compliance" of the pen mechanism (or a lead screw) and the cartridge back-end stopper to equilibrate to minimize "drool" from the needle tip upon withdrawal.

Therefore, a need exists to provide an injection pen device and method that incorporates a feature to prevent or minimize leakage of a medicament during and after delivery by ensuring accurate injection depths and optimum injection rates.

SUMMARY OF THE INVENTION

An aspect of one implementation of the present invention is to provide an injection device having a lock-out mechanism, wherein the plunger/injection mechanism of the injection device is inoperable unless a lock-out release force is applied to the proximal end of the device (such as by the application of the injection device to a skin surface). The lock-out mechanism of the device therefore prevents injection unless the needle of the device is fully seated and a lock-out release force is being applied to the skin surface.

Another aspect of one implementation of the present invention is to provide an injection device that incorporates the lock-out mechanism to ensure that proper skin contact and contact force is present prior to injection.

Another aspect of one implementation of the present invention is to provide an injection device that incorporates a rate-limiting mechanism to ensure that the delivery rate of a medicament from the device, once activated, is at an optimal rate corresponding to a receiving tissue's ability to accept the medicament.

These and other aspects are substantially achieved by providing a system and method for an injector device incorporating a lock-out mechanism designed to eliminate or minimize leakage of the medicament during and after delivery to the intradermal space. The lock-out mechanism ensures that the required needle puncture depth is realized prior to injection of the medicament by preventing, or "locking-out", the injection mechanism from advancing until a specified force is applied to the skin surface.

The injector device further incorporates a rate-limiting mechanism that is also designed to eliminate or minimize leakage of the medicament during and after delivery to the intradermal space. In one implementation of the present invention, the rate-limiting mechanism ensures that a specific rate of injection is realized during injection of the medicament by incorporating a rate limiting force mechanism (such as a spring) that is positioned in-line with the injection mechanism portion of the injector device. This rate-limiting mechanism can be set, or armed by the user to deliver a desired dosage rate via a dialing mechanism provided at a distal end of the device.

Once the lock-out release force has been achieved and the lock-out mechanism activated, the rate-limiting mechanism controls the rate at which the medicament is driven into the intradermal space by the plunger/injection mechanism of the device, and prevents the medicament from jetting back through the skin or being delivered below the desired tissue depth (that is, into the intradermal space).

Further objectives and advantages, as well as the structure and function of exemplary embodiments, will become more apparent from a consideration of the following description, drawings and examples.

BRIEF DESCRIPTION OF THE DRAWINGS

These and other objects, advantages and novel features of the invention will be more readily appreciated from the following detailed description when read in conjunction with the accompanying drawings, in which.

In the drawing figures, it will be understood that like numerals refer to like structures.

DETAILED DESCRIPTION OF THE EXEMPLARY EMBODIMENTS

Figure 1:
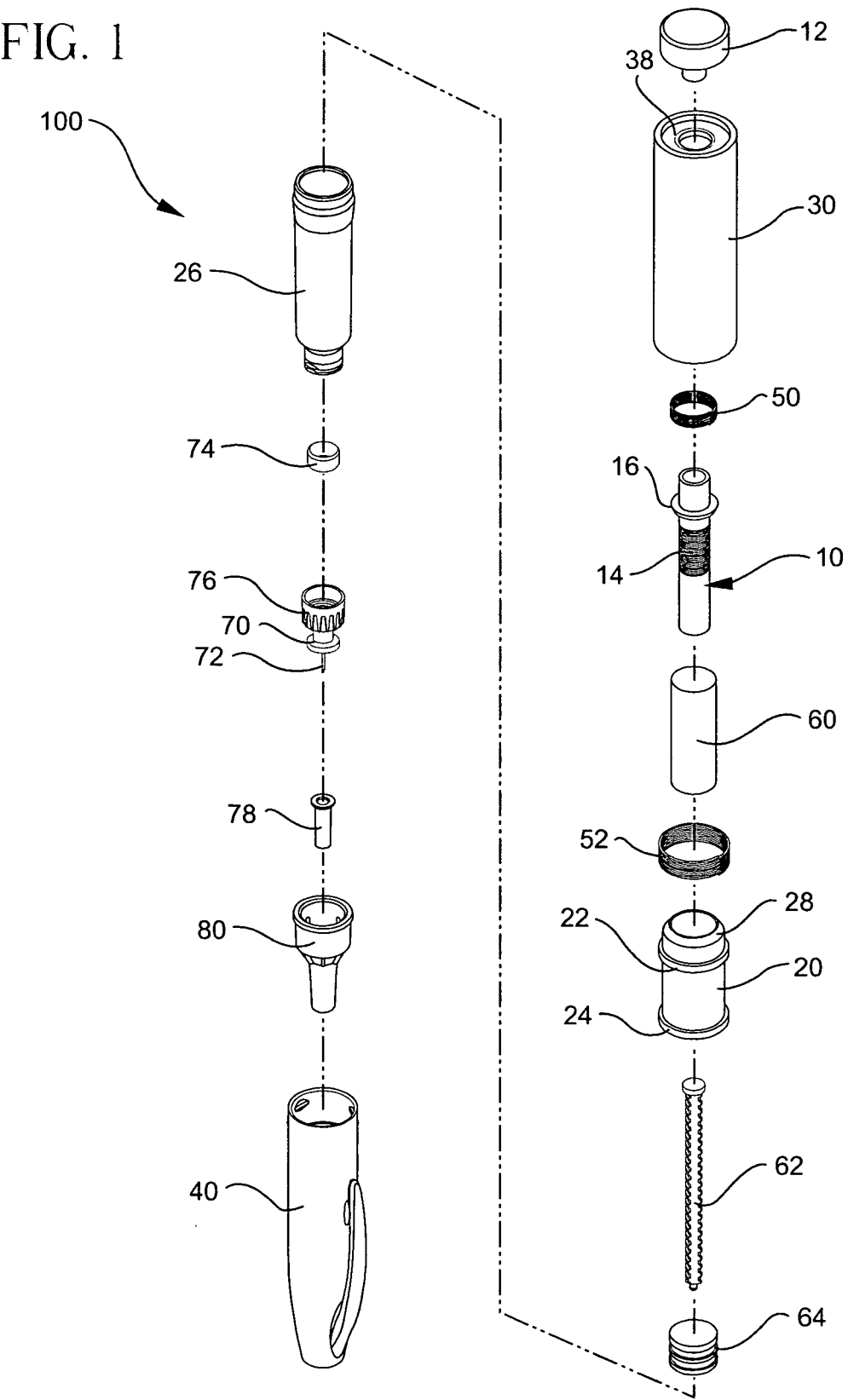
FIG. 1 is an exploded view illustrating an example of a device assembly according to an embodiment of the present invention.
Figure 2:
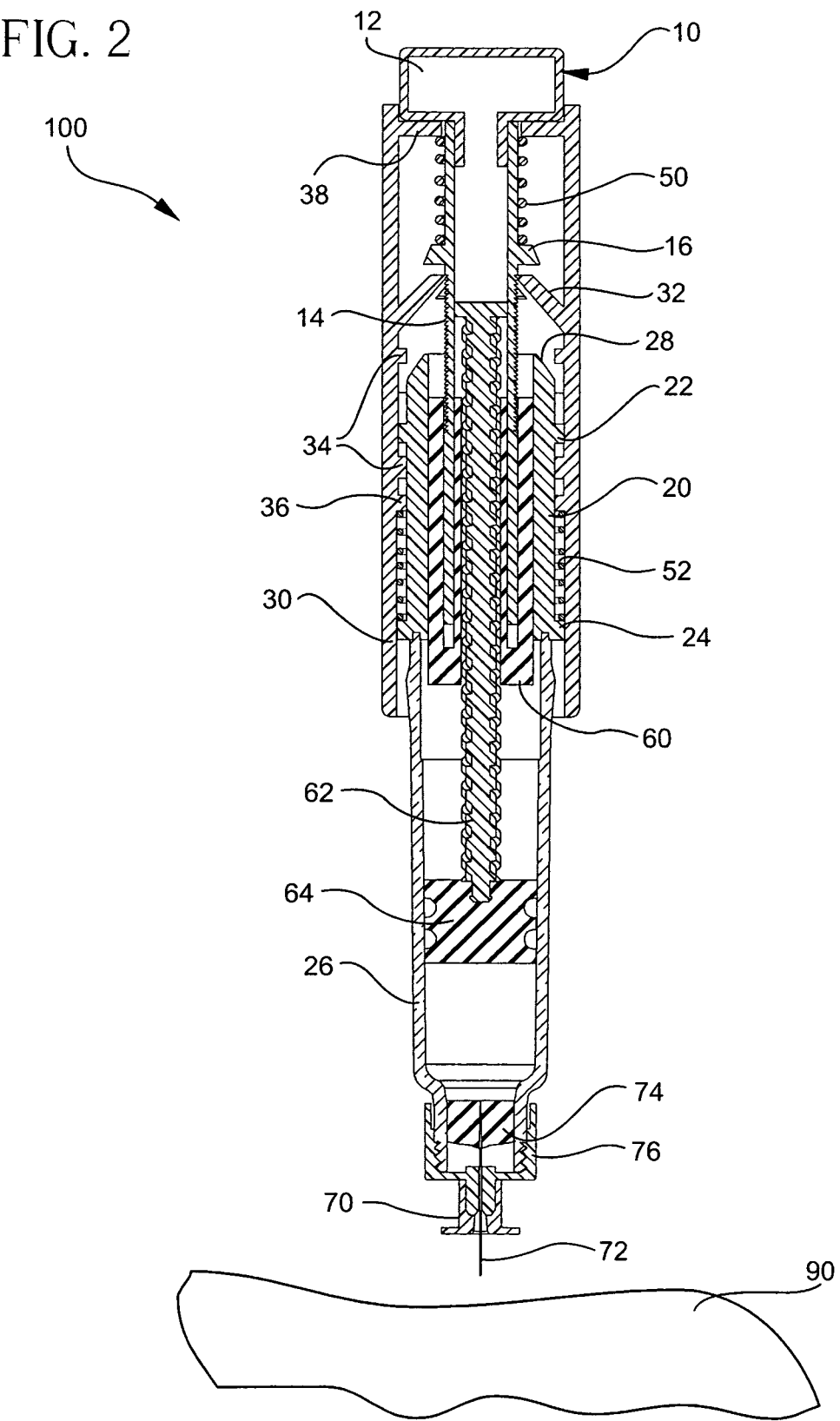
FIG. 2 is a cross-sectional side view of the device of FIG. 1 in a pre-injection position.
Figure 3:
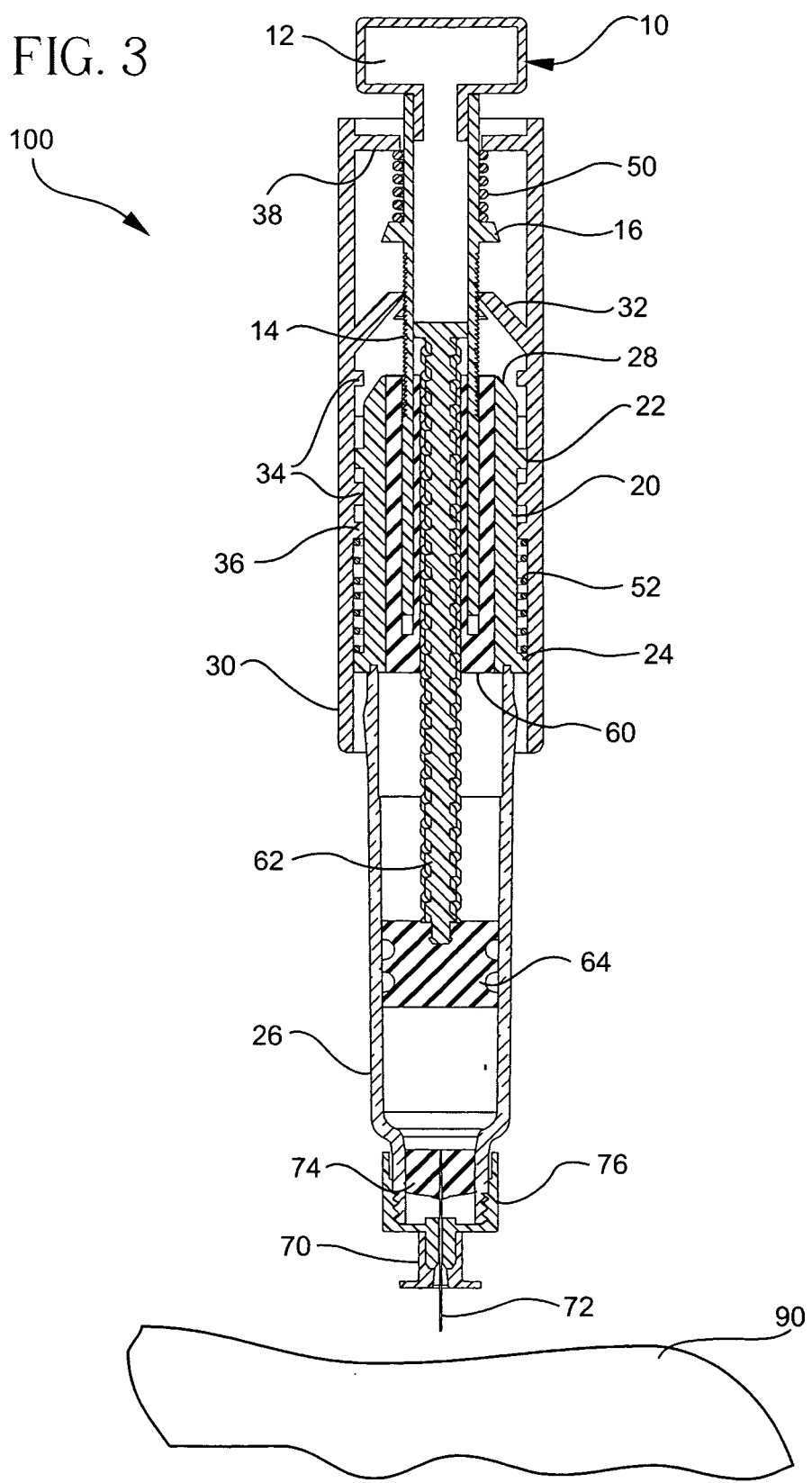
FIG. 3 is a cross-sectional side view of the device of FIG. 1 in a dialed-out, pre-injection position.
Figure 4A:
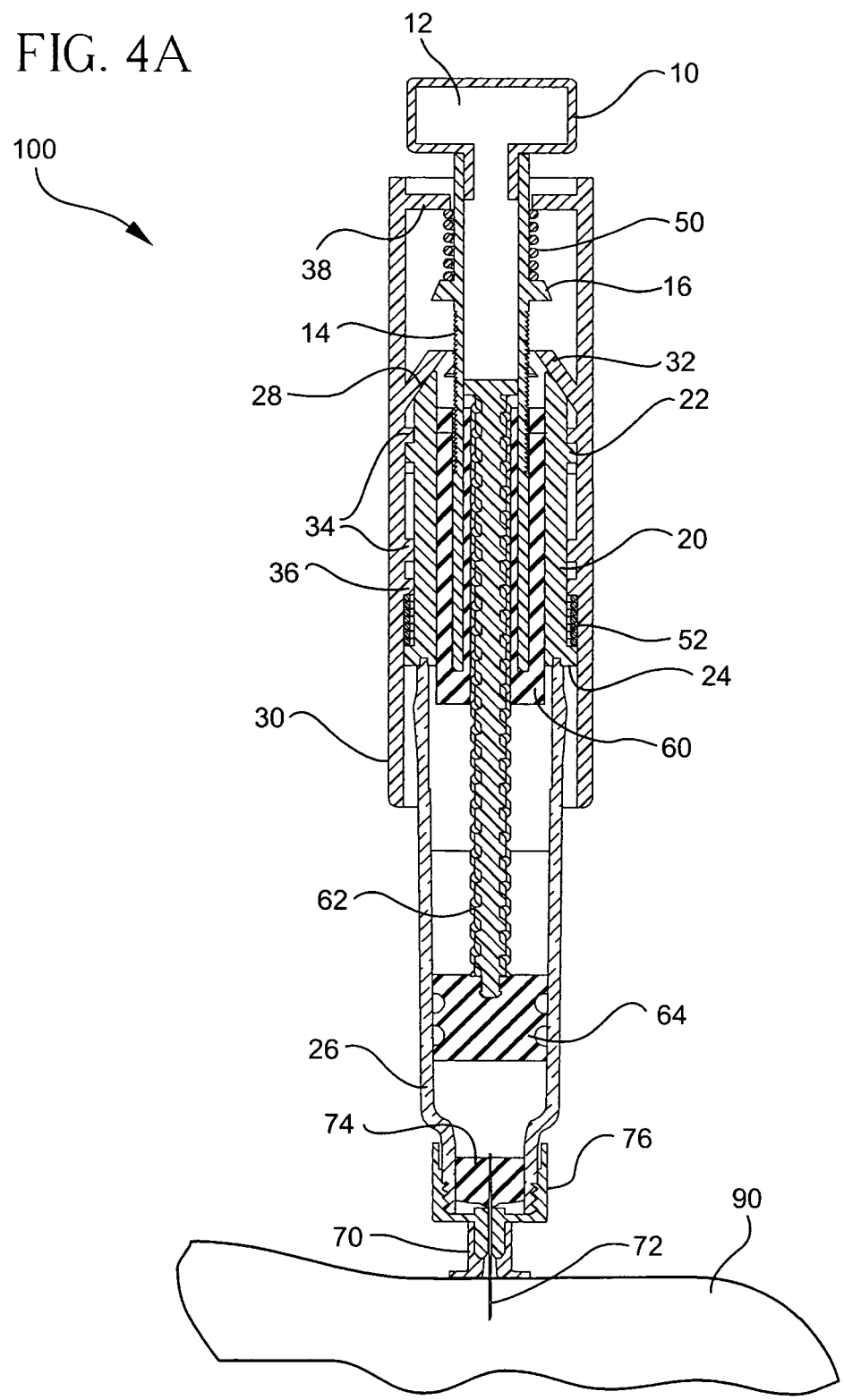
FIG. 4A is a cross-sectional side view of the device of FIG. 1 in an in-use position.
Figure 4B:
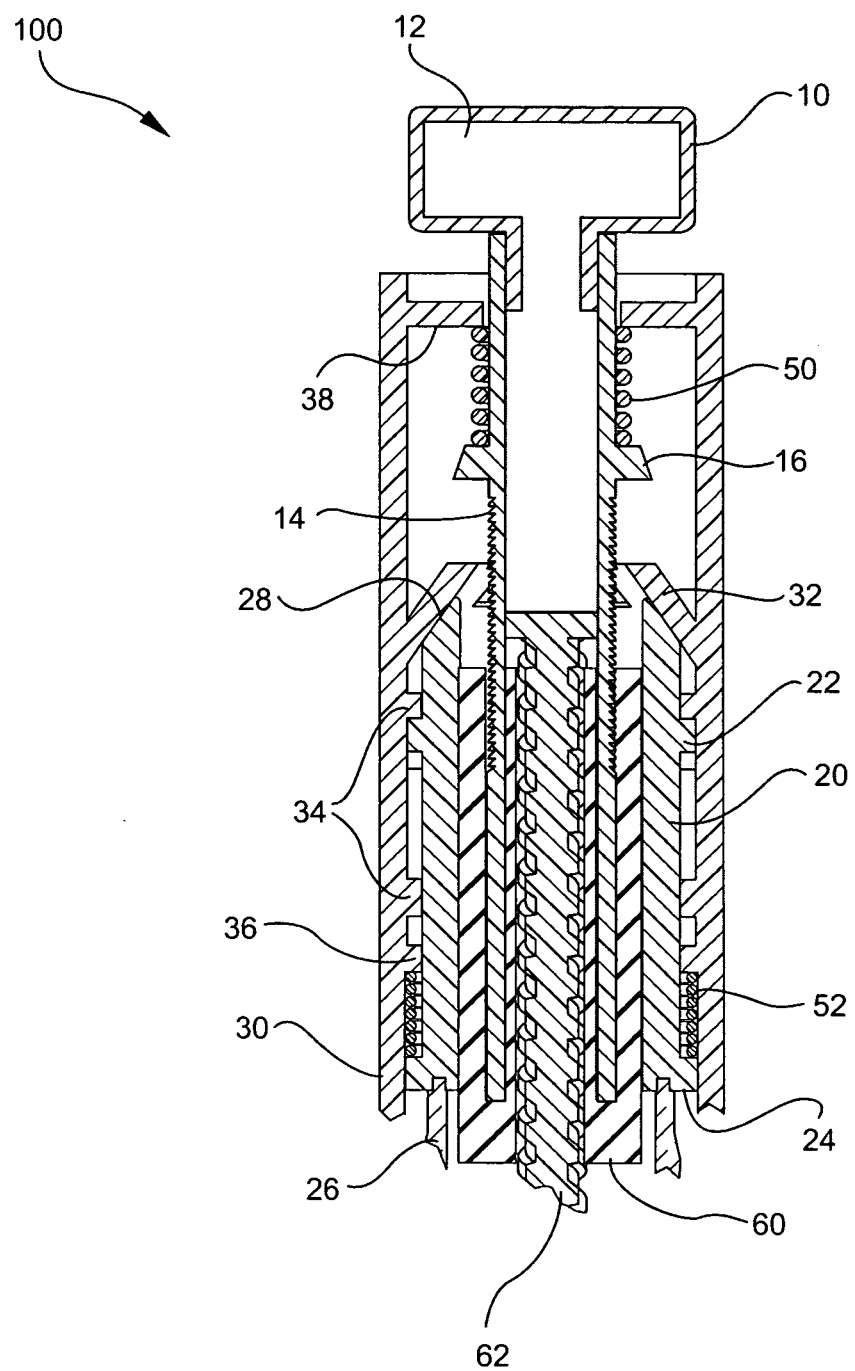
FIG. 4B is an enlarged cross-sectional side view of the compressed rate limiting and lock-out springs and disengaged ratchet arms of FIG. 4A.
Figure 5A:
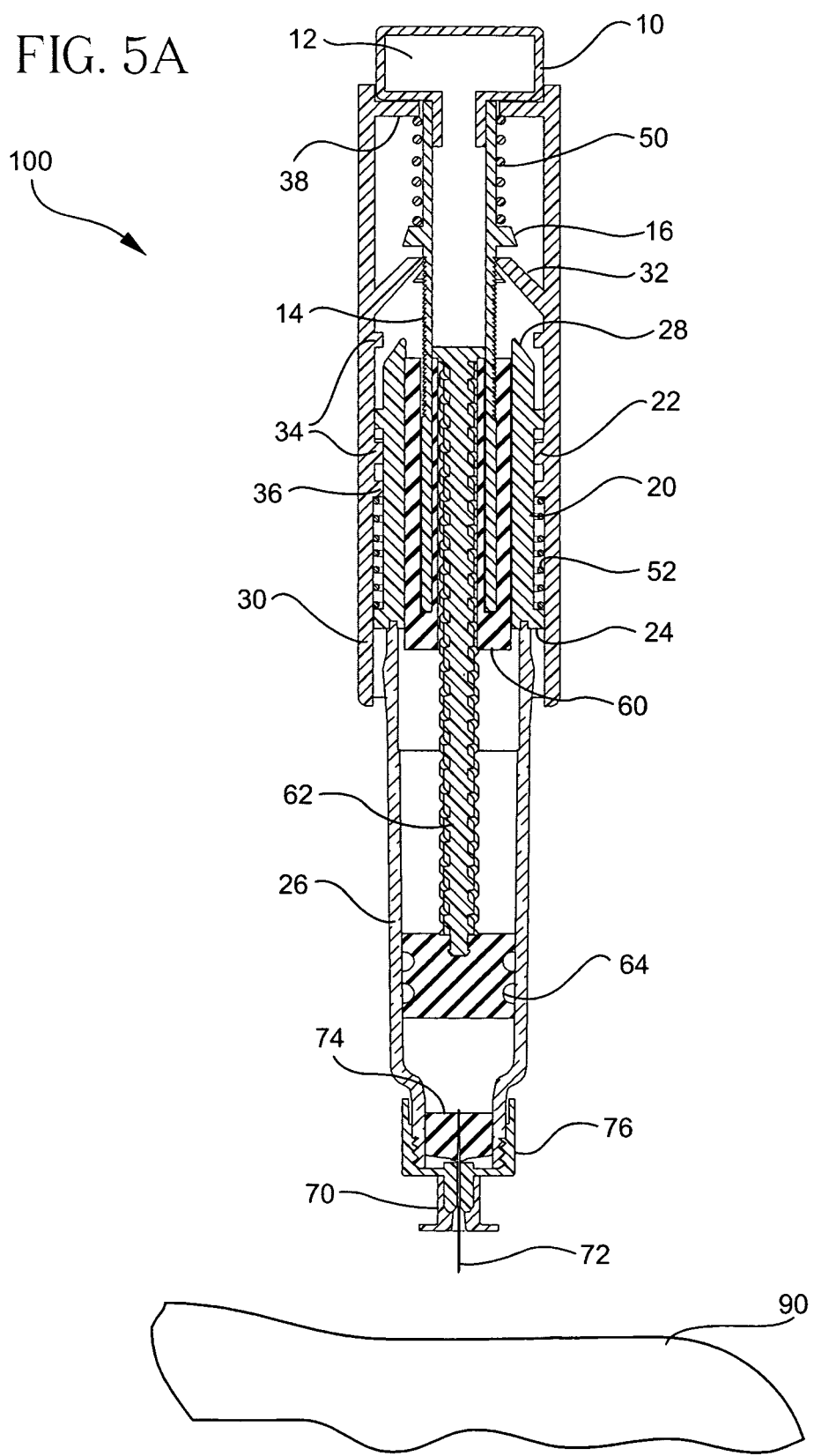
FIG. 5A is a cross-sectional side view of the device of FIG. 1 in a post-use position.
Figure 5B:
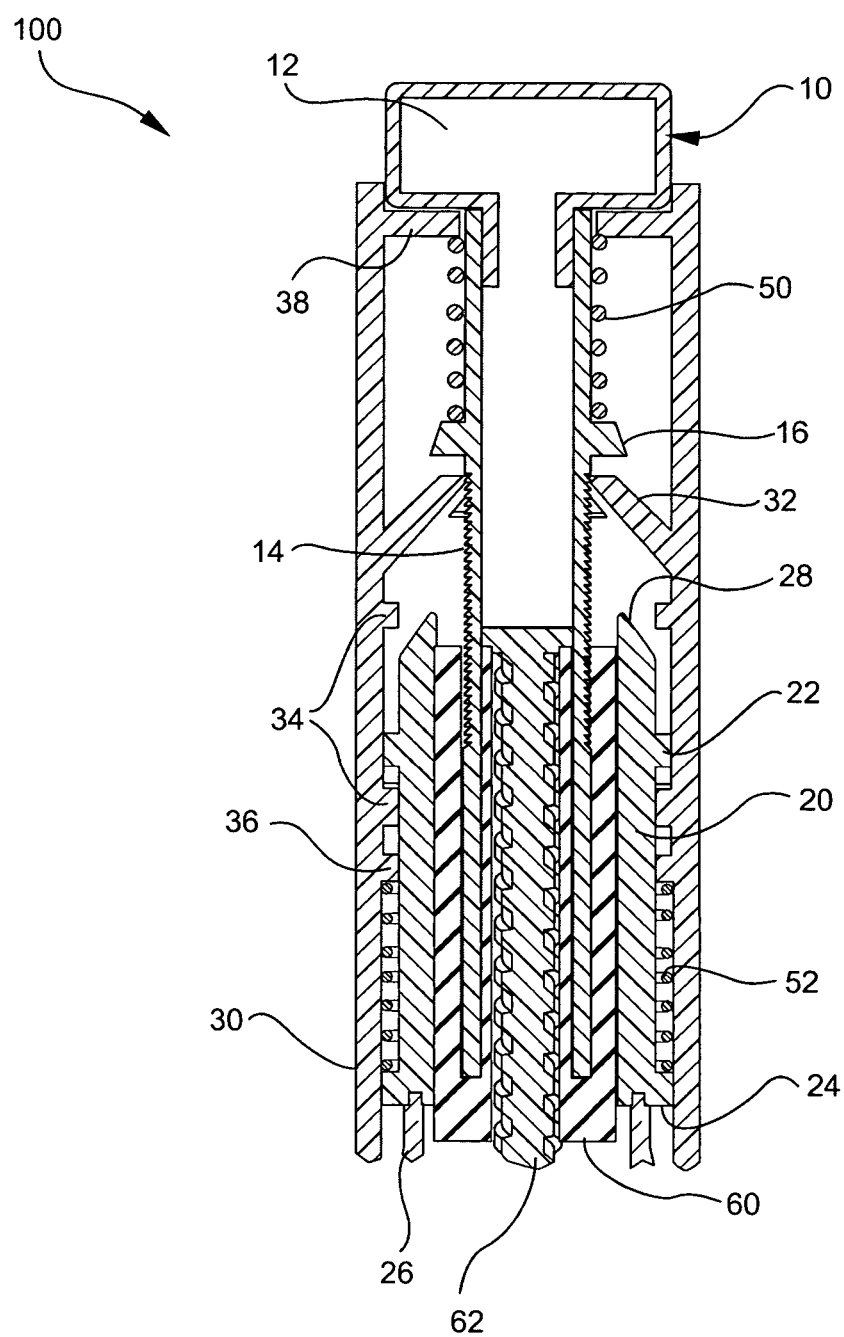
FIG. 5B is an enlarged cross-sectional side view of the released rate limiting and lock-out springs and engaged ratchet arms of FIG. 5A.
Figure 6:
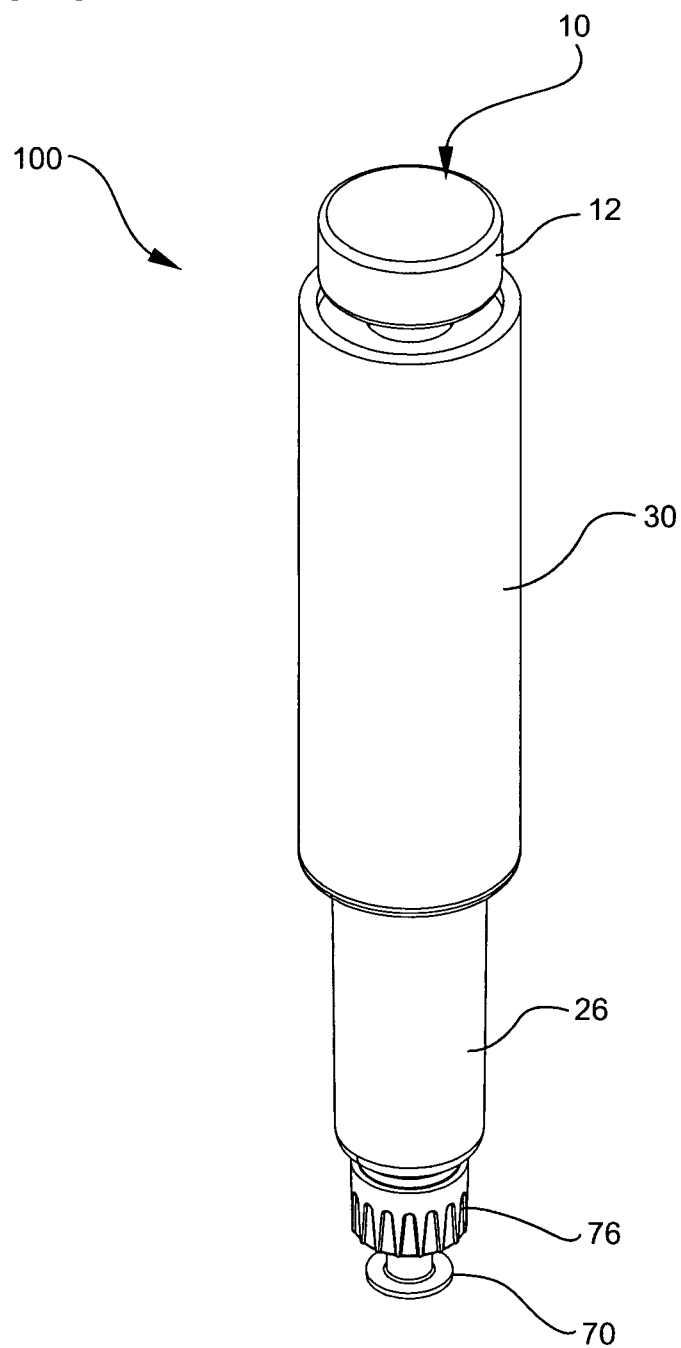
FIG. 6 is a perspective view illustrating an assembled and uncapped device according to an embodiment of the present invention.
Figure 7:
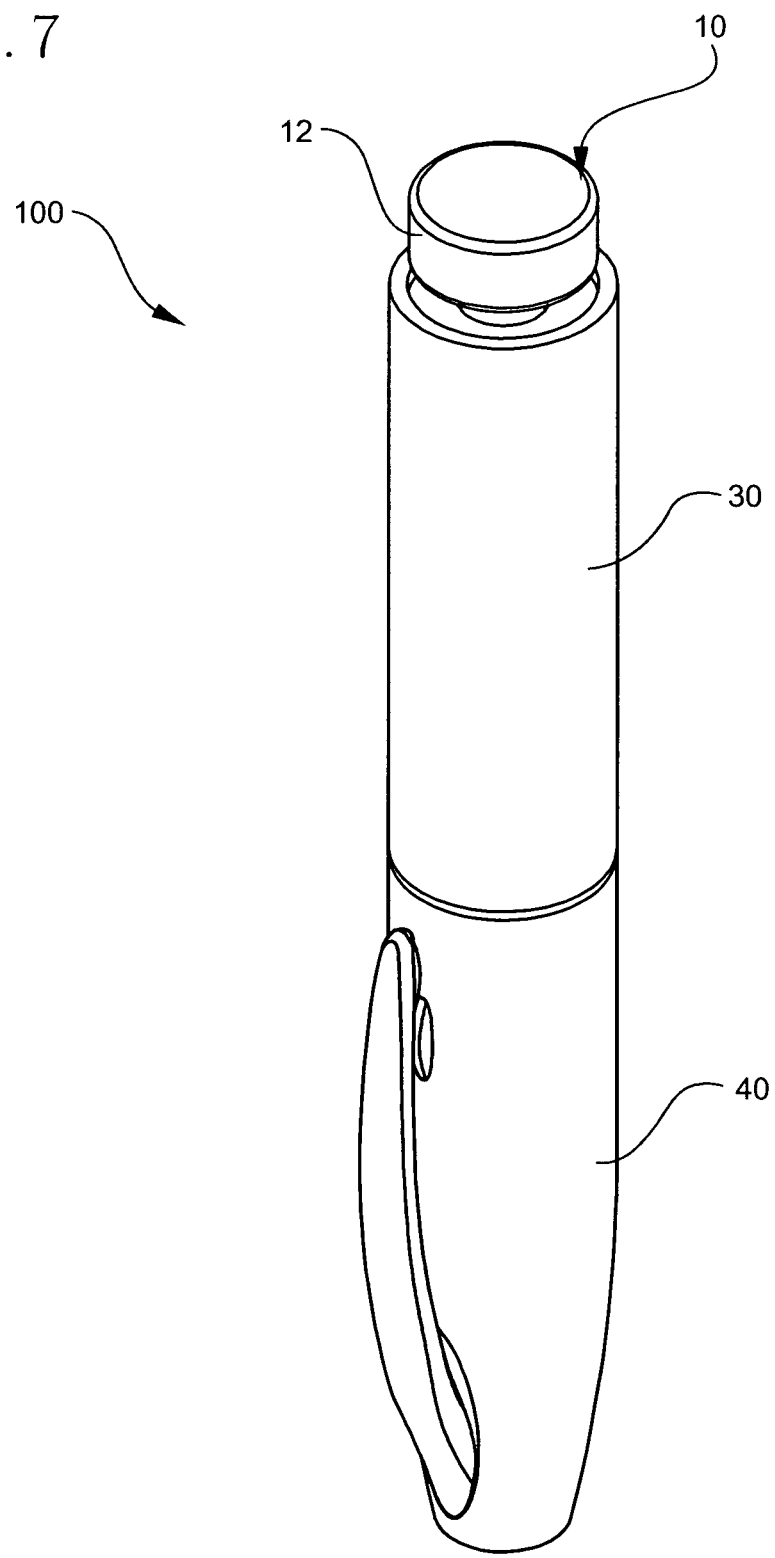
FIG. 7 is a perspective view illustrating an assembled and capped device of FIG. 1 according to an embodiment of the present invention.

In FIG. 1, an exemplary embodiment of the present invention is shown. FIG. 1 is an exploded view illustrating an example of a device assembly according to an embodiment of the present invention, and FIGS. 2 through 5 are cross-sectional side views of the device of FIG. 1 in sequential operating positions. Specifically, FIG. 2 illustrates the device in a pre-injection/dialed-in position, FIG. 3 illustrates the device in a pre-injection/dialed-out position, FIGS. 4A and 4B illustrate the device in an in-use position, and FIGS. 5A and 5B illustrate the device in a post use position. Each position is described in greater detail below. FIGS. 6 and 7 are perspective views illustrating an assembled and uncapped device, and an assembled and capped device, respectively, according to an embodiment of the present invention.

In the embodiment of the present invention shown in FIGS. 1 through 5, an injection device, exemplified by a pen injector device 100, comprises a plunger 10, a main body 20, an outer sleeve 30, and a cap 40. The device 100 further comprises a drive or rate-limiting spring 50 captured between the plunger 10 and the outer sleeve 30, and a skin pressure or lock-out spring 52 captured between the outer sleeve 30 and the main body 20.

The outer sleeve 30 further comprises a plurality of ratchet arms 32, a plurality of integral travel limits or stops 34 for defining the travel of the main body 20, an integral stop 36 to capture the lock-out spring 52, and an end member 38 to capture the rate-limiting spring 50. Disposed within the outer sleeve 30, the plunger 10 comprises a first end having a coupling mechanism for securing a plunger knob 12, a plurality of ratchet teeth 14 disposed upon an outer circumference of the plunger body for engaging the ratchet arms 32, a shoulder 16 to capture the rate-limiting spring 50, and a second end for engaging a dosing mechanism. The coupling mechanism of the plunger 10 can comprise any suitable mechanism, such as a press fit type joint, for securing the plunger knob 12 to the plunger 10. Also disposed within the outer sleeve 30, the main body 20 comprises an integral stop 22 for restricting the travel of the main body 20 to a span between stops 34, and further comprises an integral stop 24 to capture the lock-out spring 52. The main body 20 further comprises a tapered upper body surface 28 for contacting and deflecting the ratchet arms 32, and further engages a medicament cartridge 26 with an integral septum 74 at an opposite end thereof.

The device 100 further comprises a dosing mechanism housing 60, a lead screw 62, a back-end stopper 64, a needle hub 76 with an integral needle stop 70, and an intradermal pen needle 72. The needle hub 76 is secured to the medicament cartridge 26 via threads, luer lock features, or other such mechanical means of attachment. The integral needle stop 70 and intradermal pen needle 72 are secured to the medicament cartridge 26 via the needle hub 76. Once secured, the distal end of the intradermal pen needle 72 penetrates the septum 74 to provide a pathway for the desired medicament to travel from the medicament cartridge 26 to the targeted tissue, in this case, the intradermal or short subcutaneous tissue.

The main body 20 is slidably captured within the outer sleeve 30, and extends between the medicament cartridge 26 at a proximal end, and the tapered upper body surface 28 at a distal end of the main body 20. Specifically, the main body 20 comprises a cylindrical body having an outer diameter slightly less than an inner diameter of the outer sleeve 30. The main body 20 further comprises the integral stop 22 about an outer circumference, which is captured between the integral stops 34 about the inner circumference of the outer sleeve 30. Accordingly, the main body 20 is free to move within the outer sleeve 30 between the integral stops 34.

The outer sleeve 30 further houses the plunger 10, wherein the plunger 10 extends through the outer sleeve 30 and the main body 20 to engage dosing mechanisms, which comprise the dosing mechanism housing 60, lead screw 62 and back-end stopper 64. The dosing mechanisms each comprise features well known to those skilled in the art, therefore a detailed description thereof is omitted.

The plunger 10, having the plunger knob 12 which extends from the distal end of the outer sleeve 30, further captures the rate-limiting spring 50 between the end member 38 of the outer sleeve 30, and the shoulder 16 of the plunger 10. Accordingly, movement of the plunger 10 in the distal direction will compress the rate-limiting spring 50, and movement of the plunger 10 in the proximal direction will relax the rate-limiting spring 50. Further, when the rate-limiting spring 50 is compressed, the spring exerts an expansion force between the end member 38 of the outer sleeve 30 and the shoulder 16 of the plunger 10, thereby urging the plunger 10 at a limited rate in the proximal direction within the device 100. The shoulder 16 can be constructed having a small diameter and one or more beveled surfaces to facilitate assembly, but sufficiently large enough to capture the rate-limiting spring 50.

The plunger 10 further provides the plurality of ratchet teeth 14 upon an outer circumference thereof, which can engage the plurality of ratchet arms 32 of the outer sleeve 30. Specifically, the ratchet arms 32 are formed as flexible beams integral with the outer sleeve 30 and extend at an angle into the bore of the outer sleeve. By extending from the outer sleeve 30 at an angle, the flexible ratchet arms 32 can be biased toward contact with the ratchet teeth 14. Such contact between the ratchet arms 32 and the ratchet teeth 14, hereinafter referred to as an engagement between the ratchet arms 32 and the ratchet teeth 14, restricts, or locks-out movement of the plunger 10. However, by extending the flexible ratchet arms 32 from the outer sleeve 30 at an angle, the ratchet arms 32 can be easily deflected away from the ratchet teeth 14, hereinafter referred to as a disengagement between the ratchet arms 32 and the ratchet teeth 14. Accordingly, when contacted by the tapered upper body surface 28 of the main body 20 as described in greater detail below, the ratchet arms 32 can be easily deflected and disengaged from the ratchet teeth 14.

The engagement between the ratchet teeth 14 and the ratchet arms 32 restricts movement of the plunger 10 in the proximal direction. However, the engagement between the ratchet teeth 14 and the ratchet arms 32 can be configured substantially similar to that of a threaded or screw engagement, while still allowing disengagement as described above. At least one edge of each ratchet arm 32 can be inclined at an angle to mate with a similar angle provided on at least one side of each ratchet teeth 14. The angles of the ratchet arms 32 and the integral ratchet teeth 14 can be configured to act as a lock, restricting at least proximal movement of the plunger 10, and as a threaded engagement between the plunger 10 and the outer sleeve 30. That is, the ratchet arms 32 and the integral ratchet teeth 14 can perform a dual function both as threads to create linear movement of the plunger 10 when the plunger knob 12 is turned, and as a ratchet lock to otherwise prevent movement of the plunger 10 prior to disengagement.

Accordingly, the engagement between the ratchet teeth 14 and the ratchet arms 32 allows the user to "dial-in" the plunger 10 (creating proximal movement of the plunger), and "dial-out" the plunger 10 (creating distal movement of the plunger) via a turning motion of the plunger knob 12 by a user. Further, the disengagement between the ratchet teeth 14 and the ratchet arms 32, such as occurring through a deflection of the ratchet arms 32 away from the ratchet teeth 14, allows the plunger 10 to then be freely urged in the proximal direction at a limited rate by the rate-limiting spring 50.

The outer sleeve 30 further provides the integral travel limits or stops 34 protruding into the bore of the outer sleeve 30. The integral stops 34 engage the stop 22 of the main body 20 to limit movement of the main body in the distal and proximal directions within the outer sleeve 30. The limit in the distal direction coincides with the disengagement position between the ratchet teeth 14 and the ratchet arms 32 occurring through the deflection of the ratchet arms 32 away from the ratchet teeth 14 by the tapered upper body surface 28. Further, the integral stops 34 also engage the stop 22 of the main body 20 to limit movement of the main body in the proximal direction within the outer sleeve 30 as the plunger 10 is urged in the proximal direction by the rate-limiting spring 50, which in turn, urges the main body 20 in the proximal direction.

The outer sleeve 30 further provides the integral travel limit or stop 36, which functions to capture the skin pressure or lock-out spring 52 between the stop 36 of the outer sleeve 30 and the stop 24 of the main body 20. Accordingly, movement of the main body 20 in the distal direction relative to the outer sleeve 30 will function to compress the lock-out spring 52, and movement of the main body 20 in the proximal direction relative to the outer sleeve 30 will function to relax the lock-out spring 52. Accordingly, when in an exemplary use as described in greater detail below, there will typically be a movement of the main body 20 in the distal direction relative to the outer sleeve 30 and the lock-out spring 52 will be compressed as the device 100 is positioned against a skin surface 90.

When the lock-out spring 52 is compressed, the spring exerts an expansion force between the integral stop 36 of the outer sleeve 30 and the integral stop 24 of the main body 20, thereby urging the main body 20 in the proximal direction and away from the ratchet arms 32 extending into the bore of the outer sleeve 30 and allowing engagement with the ratchet teeth 14. However, contact with the skin surface 90 forces the main body 20 in the distal direction, such that the tapered upper body surface 28 of the main body 20 contacts and deflects the ratchet arms 32 away from the plunger 10, thereby disengaging the ratchet arms 32 from the ratchet teeth 14 and releasing the lock-out mechanism.

The above components provide at least two functions in the exemplary embodiments of the present invention. First, an arrangement of the above components provide a rate-limiting mechanism, and second, provide a lock-out mechanism. In an exemplary implementation illustrating the rate-limiting and lock-out mechanisms, the operation of the device 100 is shown in greater detail in association with a number of pre-use, in-use, and post-use positions. Specifically, the device 100 is first shown in a pre-injection/dialed-in position in FIG. 2, and is then shown in a pre-injection/dialed-out position in FIG. 3. The device 100 is then shown in an in-use position in FIGS. 4A and 4B, and a post use position in FIGS. 5A and 5B. Each position is described in greater detail below. FIGS. 6 and 7 are perspective views illustrating an assembled and uncapped device 100, and an assembled and capped device 100, respectively, according to an embodiment of the present invention.

Embodiments of the present invention provide an injection device 100, such as a pen injector, incorporating the lock-out mechanism designed to eliminate or minimize leakage of medicament during and after delivery to the intradermal space or any other body sites, such as the subcutaneous tissue. Leakage at the injection site typically occurs when too little force is applied to the needle stop/skin surface interface during injection. When the needle is not fully seated or is partially seated, medicament may leak back through the skin or weep out through the puncture site. Embodiments of the present invention include the lock-out mechanism to ensure that the required needle puncture depth is realized prior to injection of medicament by preventing, or locking-out, the injection mechanism such as the plunger 10 from advancing and delivering medicament until a specified force is applied to the skin surface 90. In the exemplary embodiments, this force can be between about 0.5 to about 5.0 lbs., depending on the diameter of the needle stop 70 and gauge of the needle 72 that is used. The lock-out mechanism prevents leakage at the injection site caused by too little force being applied during injection of medicament.

As noted above, certain applications can require very close depth accuracy to achieve medicament delivery within the intradermal tissue space which can be substantially achieved by providing the lock-out mechanism in accordance with an embodiment of the present invention. Certain other implementations of the present invention can further include the rate-limiting mechanism designed to further eliminate or minimize leakage of medicament during and after delivery to the intradermal space or other body sites. When the injection forces applied or injection rates employed are too high, the intradermal space (or other receiving tissue) may be unable to retain the medicament. Consequently, the medicament delivered may be "jetted" past the desired tissue depth. Delivery at a predetermined or limited rate of injection therefore, is another means to ensure depth accuracy of medicament delivery. Embodiments of the present invention can further include the rate-limiting mechanism to ensure that a specific rate of injection is realized during injection of medicament by incorporating a rate limiting force such as the rate-limiting spring 50, which is positioned in-line with the injection mechanism portion of the pen injector device 100. In an exemplary embodiment of the present invention, the rate-limiting mechanism can be set, or armed by the user to deliver a desired dosage rate via the dialing in steps outlined above.

The lock-out mechanism prevents the dosage of medicament from being administered until the injection device 100 is pressed against the skin surface 90 to a specified lock-out release force. That is, the lock-out mechanism prevents the dosage of medicament from being administered until the injection device 100 is pressed against the skin surface 90 sufficiently to force the tapered upper body surface 28 of the main body 20 into contact with the ratchet arms 32 against the resistance of the compressed lock-out spring 52, thereby disengaging the ratchet arms 32 from the ratchet teeth 14 and releasing the lock-out mechanism. If at any time, the lock-out force is not achieved or adequate pressure is not maintained, or if the injection device 100 is removed from the skin surface 90, the lock-out mechanism will re-engage and prevent the injector plunger 10 from moving, consequently preventing the dosage of medicament from being further administered.

Once the lock-out release force has been achieved, the rate-limiting mechanism then controls the delivery rate. The medicament is then driven into the intradermal space by the plunger 10, or any other suitable injection mechanism, at the controlled delivery rate provided by the rate-limiting spring 50. Delivering the medicament at a predetermined rate of injection prevents it from jetting back through the skin or being delivered below the desired tissue depth, such as into the intradermal space. Accordingly, the rate-limiting mechanism is configured based upon factors such as the type of medicament to be delivered, the desired delivery depth, the needle gauge and effective length, and the injection force and pressures required to prevent the jetting phenomenon.

In an exemplary use, the device 100 is firmly held by the outer sleeve 30 as the rate-limiting spring 50 is compressed by the user to provide a desired delivery rate. Specifically, the screw or threaded engagement between the ratchet teeth 14 and the ratchet arms 32 allows the user to "dial-out" the plunger 10 (creating distal movement of the plunger) via a turning motion of the plunger knob 12. Movement of the plunger 10 in the distal direction compresses the rate-limiting spring 50 which then exerts an expansion force between the end member 38 of the outer sleeve 30 and the shoulder 16 of the plunger 10, thereby urging the plunger 10 at a limited rate in the proximal direction within the device 100. The device 100 is then placed against the skin surface 90 of a user.

As the user firmly holds the device 100 by the outer sleeve 30 against the skin surface 90, the needle 72 seats and the needle stop 70 ensures that the correct needle depth is achieved when contacting the skin surface. At this point, the injection device 100 is pressed against the skin surface 90 sufficiently to force the tapered upper body surface 28 of the main body 20 into contact with the ratchet arms 32 against the resistance of the compressed lock-out spring 52, thereby disengaging the ratchet arms 32 from the ratchet teeth 14 and releasing the lock-out mechanism which releases the plunger 10. The plunger 10 is then driven in the proximal direction by the compressed rate-limiting spring 50 to thereby provide a correct medicament delivery rate. The operation is more clearly shown in FIGS. 2 through 5, described in greater detail below.

In FIG. 2, the device 100 of FIG. 1 is shown in a cross-sectional view in the initial pre-injection state. In this view, the skin pressure or lock-out spring 50 and the rate-limiting spring 52 are each shown in a relaxed state. Such a position may be provided for the storing of the device 100, as spring creep is eliminated.

In FIG. 3, the device 100 is shown in a cross-sectional view with the plunger knob 12 of the plunger 10 in a dialed-out state. To set the device 100 into the dialed-out state, the user can simply grasp and turn the plunger knob 12 of the plunger 10 while firmly holding the outer sleeve 30. Accordingly, turning the plunger knob 12 moves the plunger 10 in a linear direction away from the proximal end of the device 100, thereby compressing the rate-limiting spring 50. The plunger knob 12 can also be dialed-in, that is, turned such that the threaded engagement between the integral ratchet arms 32 and the integral ratchet teeth 14 moves the plunger 10 in a linear direction toward the proximal end of the device 100 should the need occur to decompress the rate-limiting spring 50.

The ratchet arms 32 restrict, or lock-out movement of the plunger 10 in the proximal direction until the ratchet arms 32 are disengaged from the integral ratchet teeth 14. Therefore, the dial-out movement of the plunger 10 is limited to the linear direction away from the proximal end of the device 100, and the plunger 10 is prevented from moving forward by the ratchet arms 32. As noted above, the dial-out movement of the plunger 10 further serves to compress the rate-limiting spring 50, which is captured between the end member 38 of the outer sleeve 30, and a shoulder 16 of the plunger 10. As the plunger 10 is retracted to a desired position, that is, retracted to a desired dialed-out state, the dialed-out plunger 10 compresses the rate-limiting spring 50. The engagement of the integral ratchet arms 32 of the outer sleeve 30 with the integral ratchet teeth 14 of the plunger 10 prevents the plunger 10 from advancing the lead screw 62 and end-stopper 64, thereby locking out the injection of medicament.

In FIG. 3, the skin pressure or lock-out spring 52 is shown in a relaxed, pre-compressed state. In FIG. 4A the skin pressure or lock-out spring 52 is shown in a compressed state. In FIGS. 4A and 4B, the device 100 is shown in a cross-sectional view with the needle stop 70 pressed against the skin surface 90 and the needle 72 penetrating the skin and into the intradermal space. In this example, while firmly holding the outer sleeve 30 of the device 100, the user applies a force toward and against the skin surface 90 of between about 0.5 to about 5.0 lbs. until the lock-out spring 52, which is captured between the stop 24 of the main body 20 and the stop 36 of the outer sleeve 30, has reached a fully loaded state or dead stop. The applied force ensures the depth accuracy of the needle 72 and medicament delivery into the desired intradermal space. This force also facilitates releasing the lock-out mechanism of the device 100, thereby allowing relative motion between the outer sleeve 30 and the plunger 10. The lock-out spring 52 captured between the outer sleeve 30 and the main body 20 substantially determines the force required to unlock the lock-out mechanism.

As shown in FIG. 4A, as the outer sleeve 30 is moved toward the skin surface 90, the tapered upper body surface 28 of the main body 20 which is stationary due to contact with the skin surface 90, comes into contact with the integral ratchet arms 32 of the outer sleeve 30 until the ratchet arms 32 are disengaged from the integral ratchet teeth 14 of the plunger 10. Once the plunger 10 becomes disengaged from the outer sleeve 30, the rate-limiting mechanism or rate-limiting spring 50 controls the rate at which the plunger 10 is depressed, and the dosed medicament can be injected at a controlled rate into an intradermal space so as to prevent a jetting phenomenon.

In FIG. 4B, the position of the device 100 in FIG. 4A is shown in a close-up cross-sectional view focusing on the lock-out mechanism and the rate-limiting spring 50. The plunger knob 12 is shown in a dialed-out state, thereby, resulting in the rate-limiting spring 50 being compressed. The potential energy stored in the rate-limiting spring 50 subsequently controls the rate at which the plunger 10 is depressed for the delivery of a dosed medicament into the intradermal space.

In FIG. 4B, the lock-out spring 52 is shown in the unlocked, or compressed state, due to the user applying a force toward and against the skin surface 90, thereby compressing the lock-out spring 52 between the moving outer sleeve 30 and the stationary main body 20. The lock-out released position is established by the relative motion between the outer sleeve 30 and the main body 20 that occurs as the device 100 is pressed against the skin surface 90.

This relative motion achieves a number of results. First, the relative motion between the outer sleeve 30 and the main body 20 disengages the integral ratchet arms 32 of the outer sleeve 30 from the integral ratchet teeth 14 on the plunger 10. This can be facilitated by providing the tapered contact surface 28 along an upper portion of the main body 20 which comes into contact with, and deflects the ratchet arms 32 away from the ratchet teeth 14 on the plunger 10. Second, an integral stop 22 extending from the main body 20, contacts the upper travel limit stop 34 integral with the inside of the outer sleeve 30 which prevents any further travel of the main body 20 away from the skin surface 90 relative to the outer sleeve 30. With the plunger 10 released from the outer sleeve 30, the rate-limiting spring 50 engages the shoulder 16 of the plunger 10 and acts to control the rate at which the plunger 10 is depressed to deliver a dosed medicament into the intradermal space to prevent the jetting phenomenon.

In FIGS. 5A and 5B, the device 100 is shown in a cross-sectional view in the post injection state. The rate-limiting spring 50 is shown in a fully unloaded state and has driven the plunger 10 to complete the dialed-in medicament dosage. Forces on the skin surface 90 have been relieved, thereby allowing the lock-out spring 52 to return to an unloaded state, and to move the main body 20 from the integral ratchet arms 32 of the outer sleeve 30. The ratchet arms 32 then re-engage with the integral ratchet teeth 14 of the plunger 10, thereby locking out further movement of the plunger 10, lead screw 62, and end-stopper 64 of the injector device 100.

The device 100 can then be secured by capping for later re-use or for disposal. FIGS. 6 and 7 are perspective views illustrating an assembled and uncapped device, and an assembled and capped device, respectively, according to an embodiment of the present invention. As shown in FIGS. 1 and 7, which equally apply to both pre-use and post-use shielding, the device 100 can further include an inner shield 78, an outer shield 80, and the cap 40 for shielding and protection purposes. The inner shield 78 and outer shield 80 can be further configured to fit an exemplary needle stop and needle hub as described in greater detail below.

Figure 8:
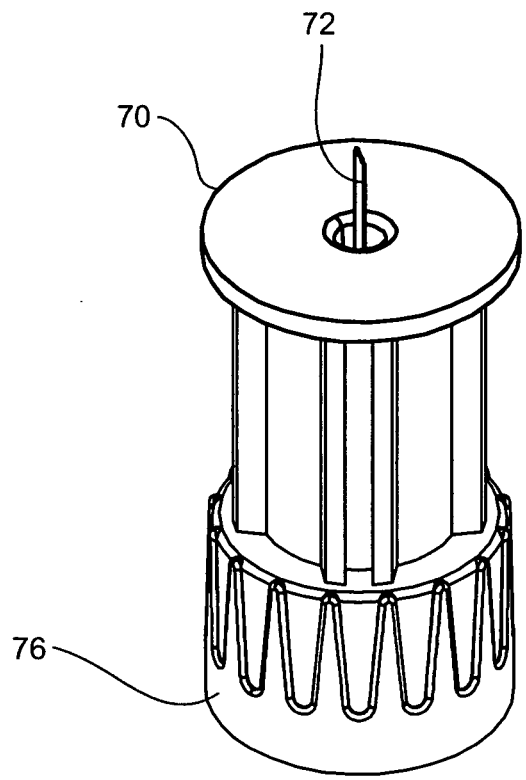
FIG. 8 is an enlarged perspective view of a needle stop for intradermal injections for use with the device of FIG. 1.

In FIG. 8, an exemplary needle stop 70 is shown integral with an intradermal needle 72 and needle hub 76. The diameter and geometry of the needle 72 and needle stop 70 can be configured in association with the lock-out spring 52 to determine a desired specified lock-out force, since excessive pressure at the site of the injection may result in discomfort to the user. The needle 72 can include any number of needle gauges, lengths and constructions. For example, needle lengths of between about 0.3 mm and about 2.0 mm are used for intradermal delivery, and needle lengths of between about 2.0 mm and about 5.0 mm are used for shallow subcutaneous delivery. These values may slightly overlap due to biological variables, such that needle lengths slightly less than 2.0 mm may be used for shallow subcutaneous delivery, and needle lengths slightly greater than 2.0 mm may be used for intradermal delivery, and so forth. The needles can be comprised of a number of materials, such as stainless steel, silicon or silicon compounds, polymers or plastics.

Figure 9:
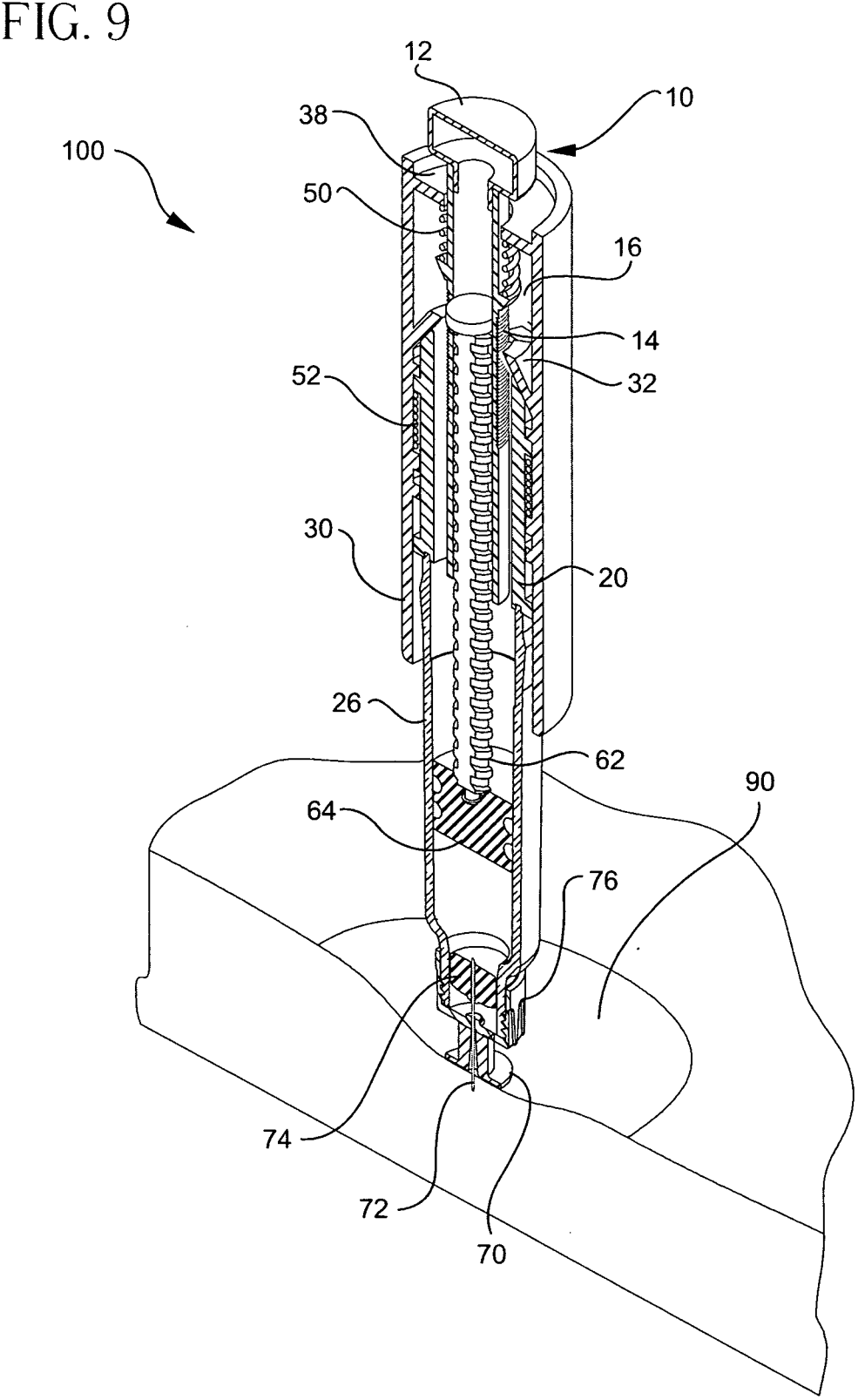
FIG. 9 is a cross-sectional perspective view of the device of FIG. 1 in use.

In FIG. 9, an in-use position of the device 100 is shown in a perspective view, similar to FIG. 4A. In FIG. 9, the pen injector device 100 is shown with the needle stop 70 pressed against the surface 90 of the skin, and the needle 72 penetrating the skin into the intradermal space. The skin can be seen to be bowing below and around the needle stop 70 due to the force applied. As noted above, the applied force can be between about 0.5 to about 5.0 lbs., and can be applied to the outer sleeve 30 to thereby compress the lock-out spring 52. In FIG. 9, the device 100 is shown to have reached a fully loaded state or dead stop, wherein the lock-out spring 52 is fully compressed. Further applied force then facilitates the unlocked position, allowing relative motion between the outer sleeve 30 and the plunger 10. Specifically, further force releases the plunger 10 from the outer sleeve 30. Once the plunger 10 is released from the outer sleeve 30, the rate-limiting spring 50 then engages the plunger 10 for controlling the rate at which the plunger 10 is depressed, and delivers a dosed medicament into the intradermal space.

The invention can be designed such that it can be configured by the end-user to the specific characteristics of the medicament being administered and the specific characteristics of the body space into which the medicament is being injected. Various drug formulations can be used with the device, such as aqueous liquids or solutions, particulate or colloidal suspensions, emulsions, gels, creams, pastes, dry solids and so forth. These various drugs can further include peptides, proteins, small organic and inorganic molecules, nucleic acids, or vaccines.

Specific embodiments may be better suited for disposable (one time use) devices, while other invention embodiments may be better suited for reusable devices, based on cost and robustness of design. Accordingly, embodiments can vary depending on whether the final device design embodiment is disposable or designed for reuse.

In still other embodiments of the present invention, other alternatives to flexing ratchet arms can include, but are not limited to, rotational ratchets, rack and pinion, elastomeric grips or donuts, halfnuts, variable contact frictional steps, ratchets on the plunger and/or on the plunger knob, lead screw/ratchet combinations, reverse rack and pinion, clutch mechanisms, ratchets engaging a lead screw, and so forth.

In the exemplary embodiments of the present invention described above, springs 50 and 52 are shown as helical compression springs, although other alternatives can include, but are not limited to, wave springs, Belleville washers, split washers, airpots, compressed liquid/gas cylinder modules, elastomeric springs, flexing beams or fingers, molded-in springs, and so forth.

Still other embodiments of the present invention can include a valve placed inline with the pen needle that only opens when the lock-out force is applied to the pen needle. Also, a visual indicator can be provided to appear on the pen injector device when the lock-out force has been achieved. This serves to alert the user as to when an adequate amount of force has been applied to the pen injector and consequently to the skin surface to permit administration of the medicament and to minimize discomfort at the injection site at the skin surface.

Embodiments of the present invention can take the form of any injection device for delivering medication or other substances into a body space or to other locations were it would be advantageous to have a leak free delivery of liquid substances. The invention is not limited solely to the delivery of medication into the intradermal space.

The exemplary lock-out and rate limiting mechanisms can be incorporated separately or in combination, into standard injection pens or other types of delivery devices, and are not limited to medicament delivery or usage in a medical device with lead screw based dosing or plunger mechanisms.

Embodiments of the present invention can further provide both improved control in achieving an optimum injection depth and in eliminating leakage during and after injection than with existing injection pen devices. These are critical improvements necessary to take full advantage of the benefits of faster uptake of medicaments delivered into the intradermal space.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims and their equivalents.

What is claimed is:

1. An injection device, comprising:
a main body extending between distal and proximal ends;
an outer sleeve disposed about said main body, said outer sleeve having an inner bore and at least one ratchet arm, wherein said at least one ratchet arm protrudes toward said inner bore of said outer sleeve, and wherein said main body is slidably disposed within said inner bore of said outer sleeve;
a plunger within said main body and said outer sleeve, and slidably engaged with said main body;
a lock-out mechanism for engagement between said outer sleeve and said plunger to restrict a linear movement of said plunger until a specified force is applied to said main body;
a rate-limiting mechanism for engagement between said outer sleeve and said plunger to control an advancement of said plunger; and
a needle for penetrating a skin surface to inject a content.

2. The injection device of claim 1, wherein said lock-out mechanism comprises:
a plurality of integral ratchet teeth disposed on said plunger for engagement with said at least one ratchet arm, wherein said engagement between said plurality of integral ratchet teeth and said at least one ratchet arm restricts a linear movement of said plunger.

3. The injection device of claim 2, wherein said engagement between said plurality of integral ratchet teeth and said at least one ratchet arm comprises a threaded engagement.

4. The injection device of claim 3, wherein said plunger further comprises a plunger knob for rotating said plunger.

5. The injection device of claim 4, wherein said threaded engagement allows a linear movement of said plunger when said plunger is rotated.

6. The injection device of claim 5, wherein said rate-limiting mechanism comprises a rate-limiting spring disposed between said plunger and said outer sleeve, wherein said rate-limiting spring is compressed through said linear movement of said plunger when said plunger is rotated.

7. The injection device of claim 6, wherein said compressed rate-limiting spring substantially determines an advancement rate of said plunger.

8. The injection device of claim 2, wherein said main body further comprises an engagement portion that moves upward to contact and deflect said at least one ratchet arm when said specified force is applied to said main body.

9. The injection device of claim 8, wherein said deflection disengages said at least one ratchet arm from said plurality of integral ratchet teeth disposed on said plunger and allows said advancement of said plunger.

10. The injection device of claim 9, wherein said lock-out mechanism further comprises a lock-out spring disposed between said main body and said outer sleeve to compress as said specified force is applied to said main body.

11. The injection device of claim 10, wherein said lock-out spring substantially determines said specified force required to disengage said lock-out mechanism.

12. The injection device of claim 1, wherein said needle comprises an intradermal pen needle.

13. The injection device of claim 1, wherein said needle comprises an integral needle stop configured for setting a desired depth for penetrating a skin surface.

14. The injection device of claim 13, further comprising a visual indicator for indicating when the specified force has been achieved.

15. The injection device of claim 1, further comprising a medicament cartridge for administering a dosage of medication.

16. An injection device, comprising:
a main body extending between distal and proximal ends;
an outer sleeve disposed about said main body, the outer sleeve having an inner bore and at least one ratchet arm, wherein said at least one ratchet arm protrudes toward said inner bore of said outer sleeve, and wherein said main body is slidably disposed within said inner bore of said outer sleeve;
a plunger within said main body and said outer sleeve, and slidably engaged with said main body;
a lock-out mechanism for engagement between said outer sleeve and said plunger to restrict a linear movement of said plunger until a specified force is applied to said main body; and
a needle for penetrating a skin surface to inject a content.

17. The injection device of claim 16, wherein said lock-out mechanism comprises:
a plurality of integral ratchet teeth disposed on said plunger for engagement with said at least one ratchet arm, wherein said engagement between said plurality of integral ratchet teeth and said at least one ratchet arm restricts a linear movement of said plunger.

18. The injection device of claim 17, wherein said main body further comprises:
an engagement portion that moves upward to contact and deflect said at least one ratchet arm when said specified force is applied to said main body, wherein said deflection disengages said at least one ratchet arm from said plurality of integral ratchet teeth disposed on said plunger and allows an advancement of said plunger.

19. The injection device of claim 17, wherein said lock-out mechanism further comprises a lock-out spring disposed between said main body and said outer sleeve to compress as said specified force is applied to said main body.

20. The injection device of claim 17, wherein said engagement between said plurality of integral ratchet teeth and said at least one ratchet arm comprises a threaded engagement.

21. The injection device of claim 20, wherein said plunger further comprises a plunger knob for rotating said plunger and creating a linear movement of said plunger.

22. The injection device of claim 21, further comprising a rate-limiting mechanism for engagement between said outer sleeve and said plunger to control an advancement of said plunger.

23. The injection device of claim 22, wherein said rate-limiting mechanism comprises a rate-limiting spring disposed between said plunger and said outer sleeve, wherein said rate-limiting spring is compressed through said linear movement of said plunger when said plunger is rotated.

24. A method for injecting medication in an injection device, comprising the steps of:
dialing in a desired measure dosage of medication in the injection device;
securing a plunger of the injection device for injecting medication using ratchet arms of an outer sleeve and preventing release of said plunger and injection until a specified force is applied by an injection needle and needle stop of a main body of said injection device against a skin surface;
slidably interposing said main body between said plunger and said outer sleeve to disengage said ratchet arms and thereby release said plunger and actuate an injection in response to said specified force being applied by the injection needle and needle stop against said skin surface and implementing an injection; and
limiting a rate of injection of said desired measure dosage of medication using a spring force between said plunger and said outer sleeve once said specified force is applied against said skin surface.

25. The method of claim 24, wherein the dialing in step further comprises the step of rotating a rate-limiting mechanism to set said desired measure dosage of medication and to set said rate of injection.

26. The method of claim 24, wherein the actuating step further comprises the step of activating a releasable lock-out mechanism by applying said specified force against said skin surface by the injection needle and needle stop.

27. An injection device, comprising:
a main body extending between distal and proximal ends;
an outer sleeve disposed about said main body and having an inner bore and at least one ratchet arm, wherein said at least one ratchet arm is disposed within said outer sleeve and protrudes into said inner bore of said outer sleeve, and wherein said main body is slidably disposed within said inner bore of said outer sleeve;
a plunger within said main body and said outer sleeve, and slidably engaged with said main body;
wherein said ratchet arm is configured to engage said plunger to restrict a linear movement of said plunger until a specified force is applied to said main body;
a first spring between said outer sleeve and said plunger to control an advancement of said plunger; and
a needle for penetrating a skin surface to inject a content.

28. The injection device of claim 27, further comprising:
a plurality of integral ratchet teeth disposed on said plunger for engagement with said at least one ratchet arm, wherein said engagement between said plurality of integral ratchet teeth and said at least one ratchet arm restricts a linear movement of said plunger.

29. The injection device of claim 28, wherein said engagement between said plurality of integral ratchet teeth and said at least one ratchet arm comprises a threaded engagement.

30. The injection device of claim 29, wherein said plunger further comprises a plunger knob for rotating said plunger.

31. The injection device of claim 30, wherein said threaded engagement allows a linear movement of said plunger when said plunger is rotated.

32. The injection device of claim 31, wherein said first spring is disposed between said plunger and said outer sleeve and is compressed through said linear movement of said plunger when said plunger is rotated.

33. The injection device of claim 32, wherein said compressed first spring substantially determines an advancement rate of said plunger.

34. The injection device of claim 28, wherein said main body further comprises an engagement portion to deflect said at least one ratchet arm when said specified force is applied to said main body.

35. The injection device of claim 34, wherein said deflection disengages said at least one ratchet arm from said plurality of integral ratchet teeth disposed on said plunger and allows said advancement of said plunger.

36. The injection device of claim 35, further comprising:
a second spring disposed between said main body and said outer sleeve to compress as said specified force is applied to said main body.

37. The injection device of claim 36, wherein said second spring substantially determines said specified force required to disengage said at least one ratchet arm from said plurality of integral ratchet teeth disposed on said plunger and allows said advancement of said plunger.

38. The injection device of claim 27, wherein said needle comprises an intradermal pen needle for penetrating a skin surface to inject a content into an intradermal tissue space.

39. The injection device of claim 27, wherein said needle comprises an integral needle stop for setting a desired depth for penetrating a skin surface.

40. The injection device of claim 39, further comprising a visual indicator for indicating when the specified force has been achieved.

41. The injection device of claim 27, further comprising a medicament cartridge for administering a dosage of medication.

42. An injection device, comprising:
   a main body extending between distal and proximal ends;
   an outer sleeve disposed about said main body, said outer sleeve having an inner bore and at least one ratchet arm, wherein said at least one ratchet arm protrudes toward said inner bore of said outer sleeve, and wherein said main body is slidably disposed within said inner bore of said outer sleeve;
   a plunger within said main body and said outer sleeve, and slidably engaged with said main body; and
   a needle for penetrating a skin surface to inject a content;
   wherein said ratchet arm is configured to engage said plunger to restrict a linear movement of said plunger until a specified force is applied to said main body.

43. The injection device of claim 42, further comprising:
   a plurality of integral ratchet teeth disposed on said plunger for engagement with said at least one ratchet arm, wherein said engagement between said plurality of integral ratchet teeth and said at least one ratchet arm restricts a linear movement of said plunger.

44. The injection device of claim 43, wherein said proximal end of said main body is configured to deflect said at least one ratchet arm when said specified force is applied to said main body, wherein said deflection disengages said at least one ratchet arm from said plurality of integral ratchet teeth disposed on said plunger and allows an advancement of said plunger.

45. The injection device of claim 43, further comprising a first spring disposed between said main body and said outer sleeve to compress as said specified force is applied to said main body.

46. The injection device of claim 43, wherein said engagement between said plurality of integral ratchet teeth and said at least one ratchet arm comprises a threaded engagement.

47. The injection device of claim 46, wherein said plunger further comprises a plunger knob for rotating said plunger and creating a linear movement of said plunger.

48. The injection device of claim 47, further comprising a second spring between said outer sleeve and said plunger to control an advancement of said plunger.

49. The injection device of claim 48, wherein said second spring is compressed through said linear movement of said plunger when said plunger is rotated.

* * * * *